United States Patent [19]

Rene et al.

[11] Patent Number: 5,082,666

[45] Date of Patent: Jan. 21, 1992

[54] PROCESS FOR PREPARING SOLUBLE AND/OR SPLITABLE TABLETS AND TABLETS THUS OBTAINED

[75] Inventors: Michel Rene, Paris; Jean-Claude Plantefeve, Vernouille, both of France

[73] Assignee: Laboratoires Beaufour, France

[21] Appl. No.: 441,185

[22] Filed: Nov. 22, 1989

Related U.S. Application Data

[63] Continuation of Ser. No. 103,175, Sep. 30, 1987, abandoned.

[30] Foreign Application Priority Data

Oct. 14, 1986 [GB] United Kingdom ............... 8624628

[51] Int. Cl.$^5$ ............................................... A61K 9/44
[52] U.S. Cl. ............................................... 424/467
[58] Field of Search ............... 424/464, 465, 467, 468, 424/470, 496

[56] References Cited

U.S. PATENT DOCUMENTS

| | | | |
|---|---|---|---|
| 4,134,943 | 1/1979 | Knitsch et al. | 264/28 |
| 4,668,514 | 5/1987 | Micetich et al. | 424/114 |
| 4,729,895 | 3/1988 | Makino et al. | 424/465 |

*Primary Examiner*—Margaret B. Medley
*Attorney, Agent, or Firm*—Lucas & Just

[57] ABSTRACT

This invention relates to a process for the preparation of tablets readily soluble and/or splitable in water comprising introducing, into the preparation ready to be pressed, a sufficient amount of a liquid agent having a boiling point between 35° C. and +50° C. selected from within the halogenated hydrocarbons or mixtures thereof, proceeding with the comprising step and, finally, eliminating the volatile liquid which leads to a porous structure.

3 Claims, No Drawings

PROCESS FOR PREPARING SOLUBLE AND/OR SPLITABLE TABLETS AND TABLETS THUS OBTAINED

This is a continuation of application Ser. No. 103,175, filed Sept. 30, 1987, now abandoned.

The invention relates to a process for preparing readily soluble and/or splitable moulded compositions, such as tablets, and to the products thus obtained. Such tablets are useful in various cases such as, for instance, for sweetening agents (sugar or sugar substitutes) or for drugs.

Effervescent tablets and preparations are well known forms of presentation of pharmaceutical specialties. Generally, there is some delay in their dissolution or splitting. Moreover, effervescent tablets generally contain a substantial amount of sodium usually in the form of sodium bicarbonate. The presence of sodium is preferably to be avoided for patients suffering from circulatory disorders and/or cardiac maladies. Various attempts to provide sodium free effervescent tablets without using freezing or lyophilisation techniques have, so far, not succeeded. The state of the art in this field may be exemplified by French patent publication Nos. 2 199 973 and 2 335 205. The products obtained according to the first document are described as unsatisfactory by the second (page 2 lines 26-30). Indeed, it would be of special interest not merely to eliminate sodium from such tablets but to eliminate all metallic cations while retaining the property of rapid dissolution or splitting in the presence of water.

The invention provides a process for the preparation of tablets readily soluble and/or splitable in water, the process comprising introducing, into the preparation ready to be pressed or moulded, a sufficient amount of a liquid agent boiling between $-35°$ C. and $+50°$ C., the agent being selected from within the halogenated hydrocarbons or mixtures thereof, proceeding with the moulding or compressing step and, finally, eliminating the volatile liquid agent either slowly at room temperature or by gentle warming or by lowering the pressure or by both gentle warming and lowering of the pressure, with the proviso that the selected agent should be insoluble or poorly soluble in the components of the preparation to be moulded and should not react with or be firmly absorbed by the same.

The advantages of using a liquid which is practically a non-solvent of the components are the prevention of the sticking of the components to the mould and of a correlative deposit of the same and the possible suppression of a conventional lubricating agent due to the specific lubricating action of this liquid.

The selected agent should be introduced in the feeding device of the moulding unit or at any appropriate level in the mould.

The agent may be slowly eliminated at room temperature for agents boiling under the same or slightly over which gives a product with a porous structure; if necessary, a moderate warming of the compressed products by any usual method and/or submitting them to a reduced pressure will be used.

Preferred volatile liquid agents are the non-flammable mono- or poly-halosubstituted hydrocarbons such as trichlorofluoromethane, difluorochlorobromomethane, trichlorotrifluoroethane, tetrafluorodichloroethane and dichloromethane or mixtures thereof.

As the readily soluble and/or splitable tablets obtained according to the invention are generally dissolved and/or split very fast, the invention might also be used to speed the dissolution of conventional effervescent tablets.

A particular advantage of the invention is that it can be performed easily in conventional tablet-moulding units fitted with appropriate extra means for injection of the agent and for its elimination with a possible recovering of the same in a drying step. This is a particularly strong advantage when it is considered that sophisticated freezing and warming equipments are needed to prepare readily soluble compositions by the lyophilisation methods.

The invention also provides for the tablets or analogs obtained according to the aforementioned process; such tablets may easily be identified by the analytical identification of traces of the volatile agent used.

Some examples of preparations obtained according to the invention are given below.

EXAMPLE 1

Sweetening tablets

| | |
|---|---|
| N-L-α-Aspartyl-L-phenylalanine methyl ester | 0.020 g |
| Lactose | 0.280 g |
| For one tablet finished at: | 0.300 g |
| Dichloromethane | 0.4 ml |

Elimination at 60°-70° C. for half an hour.

EXAMPLE 2

Sodium cyclamate tablets

| | |
|---|---|
| Sodium cyclamate | 0.050 g |
| Mannitol | 0.350 g |
| For one tablet finished at: | 0.400 g |
| Trichlorofluoromethane (F11) | 0.5 ml |

Elimination at 50° C. about 40 minutes.

EXAMPLE 3

Saccharin sodium tablets

| | |
|---|---|
| Saccharin sodium | 0.010 g |
| Lactose | 0.190 g |
| For one tablet finished at: | 0.200 g |
| Trichlorofluoromethane (F11) | 0.1 ml |

Elimination at room temperature for 25 minutes.

EXAMPLE 4

Monoammonium glycyrrhizinate tablets

| | |
|---|---|
| Monoammonium glycyrrhizinate | 0.050 g |
| Mannitol | 0.250 g |
| Lactose | 0.200 g |
| For one tablet finished at | 0.500 g |
| Trichlorofluoromethane (F11) | 0.2 ml |
| +Dichlorotetrafluoroethane (F114) | 0.2 ml |
| | 0.4 ml |

Elimination at 50° C. between 30 and 40 minutes.

EXAMPLE 5

| Betaine Citrate | 2.000 g |
|---|---|
| Sodium bicarbonate | 0.450 g |
| Citric anhydrous acid | 0.050 g |
| Polyoxyethyleneglycol 6.000 | 0.060 g |
| Sodium saccharinate | 0.010 g |
| Lemon flavour | 0.002 g |
| Orange flavour | 0.005 g |
| Sorbitol | 1.000 g |
| Mannitol | 2.423 g |
| For one tablet finished at | 6.000 g |
| Trichlorofluoromethane (F11) | 2.5 ml |

Elimination at room temperature for 12 hours.

EXAMPLE 6

Aluminium hydroxide and magnesium carbonate gel tablets

| Aluminium hydroxide and magnesium co-dried carbonate gel | 0.300 g |
|---|---|
| Mannitol | 0.290 g |
| Aspartame | 0.010 g |
| For one tablet finished at: | 0.600 g |
| Trichlorofluoromethane (F11) | 0.2 ml |
| +Trichlorotrifluoroethane (F113) | 0.2 ml |
| | 0.4 ml |

Elimination at 60°–70° C. for one hour.

EXAMPLE 7

Acetylsalicylic acid tablets

| Acetylsalicylic acid | 0.500 g |
|---|---|
| Wheat starch | 0.070 g |
| Mannitol | 0.230 g |
| For one tablet finished at: | 0.800 g |
| Trichlorofluoromethane (F11) | 0.3 ml |
| +Dichlorotetrafluoroethane (F114) | 0.1 ml |
| | 0.4 ml |

Elimination either at room temperature in about 24 hours or at 50° C. in about five minutes (I.R. warming).

EXAMPLE 8

Ginkgo, heptaminol chlorhydrate and troxerutine extract soluble tablets

| Ginkgo Biloba extract | 0.014 g |
|---|---|
| Heptaminol chorhydrate | 0.300 g |
| Troxerutine | 0.300 g |
| Silicic acid | 0.002 g |
| Polyoxyethyleneglycol 6.000 | 0.022 g |
| Mannitol | 0.262 g |
| For one tablet finished at: | 0.900 g |
| Trichlorotrifluoroethane (F113) | 0.5 ml |

Elimination at 60°–70° C. for one hour

EXAMPLE 9

Smectite tablets

| Smectite | 2.500 g |
|---|---|
| Sodium saccharinate | 0.010 g |
| Mannitol | 2.490 g |
| For one tablet finished at: | 5.000 g |
| Trichlorofluoromethane (F11) | 1 ml |

Elimination at 50° C. for one hour.

EXAMPLE 10

Ginkgo extract soluble tablets

| Ginkgo Biloba extract | 0.040 g |
|---|---|
| Mannitol | 0.653 g |
| Sodium saccharinate | 0.005 g |
| Orange flavour | 0.002 g |
| For one tablet finished at: | 0.700 g |
| Trichlorofluoromethane (F11) | 0.5 ml |

Elimination at room temperature in about 24 hours or at 50° C. in about five minutes (I.R. warming).

EXAMPLE 11

Vitamin C soluble tablets

| Ascorbic acid | 0.250 g |
|---|---|
| Mannitol | 0.350 g |
| Monohydrated lactose | 0.100 g |
| For one tablet finished at: | 0.700 g |
| Trichlorotrifluoroethane (F113) | 0.2 ml |
| +Dichlorotetrafluoroethane (F114) | 0.2 ml |
| | 0.4 ml |

Elimination at 60°–70° C. for one hour.

EXAMPLE 12

Vitamin C soluble tablets

| Ascorbic acid | 0.100 g |
|---|---|
| Mannitol | 0.300 g |
| For one tablet finished at: | 0.400 g |
| Trichlorotrifluoroethane (F113) | 0.5 ml |

Elimination at 60°–70° C. for one hour.

EXAMPLE 13

Antiacid and absorbing tablets

| Montmorillonite | 0.800 g |
|---|---|
| Magnesium phosphate (5 $H_2O$) | 0.200 g |
| For one tablet finished at: | 1.000 g |
| Trichlorofluoromethane (F11) | 0.2 ml |
| +Dichlorotetrafluoroethane (F114) | 0.2 ml |
| | 0.4 ml |

Elimination at 60°–70° C. for one hour.

EXAMPLE 14

Aluminium hydroxide and magnesium hydroxide tablets

| Aluminium hydroxide | 0.250 g |
|---|---|
| Magnesium hydroxide | 0.250 g |
| Lactose | 0.197 g |
| Sorbitol | 0.200 g |
| Acid saccharinate | 0.003 g |
| For one tablet finished at: | 0.900 g |
| Dichloromethane | 0.6 ml |

Elimination at 60°–70° C. for one hour.

EXAMPLE 15

Ginkgolides tablets

| | |
|---|---|
| Ginkgolide A + B + C | 0.040 g |
| Lactose | 0.260 g |
| For one tablet finished at: | 0.300 g |
| Trichlorofluoromethane (F11) | 0.45 ml |

Elimination at room temperature in about 24 hours or at 50° C. in about five minutes (I.R. warming).

EXAMPLE 16

Bromomethyloxine tablets

| | |
|---|---|
| Bromomethyloxine | 0.033 g |
| Colloidal silica | 0.117 g |
| For one tablet finished at: | 0.150 g |
| Trichlorofluoromethane (F11) | 0.2 ml |

Elimination at 50° C. for half an hour.

We claim:

1. A process for the preparation of tablets from a mixture of components which are readily soluble and/or splitable in water comprising selecting a volatile liquid agent having a boiling point between $-35°$ C. and $+50°$ C., said agent being a halogenated hydrocarbon or a mixture of halogenated hydrocarbons, said agent being insoluble or poorly soluble in said components, and said agent not reacting with or being firmly absorbed by said components, introducing said agent into the preparation ready to be pressed or moulded in an amount sufficient to make a tablet which is readily soluble, splitable, or both, thereafter proceeding with the moulding or compressing step and, finally, after the moulding or compressing step, eliminating the volatile liquid agent either slowly at room temperature or by gentle warming or by lowering the pressure or by both gentle warming and lowering of the pressure.

2. The process of claim 1 wherein the volatile liquid agent is a non-flammable mono- or poly-halosubstituted hydrocarbon or a mixture thereof.

3. The process of claim 2 wherein the volatile liquid agent is trichlorofluoromethane, difluorochlorobromomethane, trichlorotrifluoroethane, tetrafluorodichloroethane, dichloromethane or a mixture thereof.

* * * * *